(12) United States Patent
Rossi et al.

(10) Patent No.: US 9,730,458 B2
(45) Date of Patent: Aug. 15, 2017

(54) TREATMENT OF CEREAL FLOUR AND SEMOLINA FOR CONSUMPTION BY CELIAC PATIENTS

(75) Inventors: Mauro Rossi, Avellino (IT); Carmela Gianfrani, Naples (IT); Rosa Anna Siciliano, Avellino (IT)

(73) Assignee: Consiglio Nazionale Delle Ricerche, Rome (IT)

(*) Notice: Subject to any disclaimer, the term of this patent is extended or adjusted under 35 U.S.C. 154(b) by 659 days.

(21) Appl. No.: 12/312,240

(22) PCT Filed: Oct. 29, 2007

(86) PCT No.: PCT/IB2007/003245
§ 371 (c)(1),
(2), (4) Date: Apr. 30, 2009

(87) PCT Pub. No.: WO2008/053310
PCT Pub. Date: May 8, 2008

(65) Prior Publication Data
US 2010/0221384 A1    Sep. 2, 2010

(30) Foreign Application Priority Data

Oct. 30, 2006 (IT) .............................. MI2006A2080

(51) Int. Cl.
*A21D 6/00* (2006.01)
*A21D 2/26* (2006.01)
(Continued)

(52) U.S. Cl.
CPC ............. *A21D 2/268* (2013.01); *A21D 2/265* (2013.01); *A21D 6/00* (2013.01); *A23J 3/346* (2013.01);
(Continued)

(58) Field of Classification Search
CPC .......... A21D 2/265; A21D 2/268; A21D 6/00; C12Y 203/02013; A23L 1/0153; A23L 1/1055
(Continued)

(56) References Cited

U.S. PATENT DOCUMENTS

2002/0061344 A1    5/2002  Schuhmann

FOREIGN PATENT DOCUMENTS

DE          10346764       4/2004
EP          0333528        9/1989
(Continued)

OTHER PUBLICATIONS

Schrode et al, Stereochemcial Aspects of Amine Substrate Attachmnent to Acyl Intermediates of Transglutaminases, Journal of Biological Chemistry, vol. 254, No. 3, Issue of Feb. 10, pp. 653-661, 1979.*

(Continued)

*Primary Examiner* — D. Lawrence Tarazano
*Assistant Examiner* — Philip Dubois
(74) *Attorney, Agent, or Firm* — Stetina Brunda Garred & Brucker

(57) ABSTRACT

The present invention relates to the use of an enzymatic method for treating flour, semolina and protein extracts derived from cereals known to stimulate a pathological immune response in patients affected by Celiac Disease (CD). Said treatment drastically reduces or completely eliminates the toxicity of gluten or similar products derived from other cereals. The method uses the catalytic activity of microbial transglutaminase and, in particular, its ability to bind proteins in cereal flour or semolina to an alkylated ($C_1$-$C_4$) derivative of lysine. After the treatment said pro- (Continued)

teins extracted from flour show a substantially lowered immuno-stimulatory activity in celiac patients T lymphocytes.

13 Claims, 2 Drawing Sheets

(51) Int. Cl.
- *A23J 3/34* (2006.01)
- *A23L 5/20* (2016.01)
- *A23L 7/104* (2016.01)
- *A23L 33/18* (2016.01)
- *A21D 2/00* (2006.01)

(52) U.S. Cl.
CPC .................. *A23L 5/25* (2016.08); *A23L 7/107* (2016.08); *A23L 33/18* (2016.08); *C12Y 203/02013* (2013.01)

(58) Field of Classification Search
USPC .......................................................... 426/18
See application file for complete search history.

(56) References Cited

FOREIGN PATENT DOCUMENTS

| | | |
|---|---|---|
| EP | 0685164 | 12/1995 |
| EP | 0745670 | 12/1996 |
| EP | 0847701 | 6/1998 |
| EP | 0870434 | 10/1998 |
| EP | 0938845 | 9/1999 |
| EP | 1085023 | 3/2001 |
| JP | 58023234 | 2/1983 |
| JP | 079707 | 3/1995 |
| WO | WO99/56698 | * 11/1999 |
| WO | WO 9956698 | 11/1999 |
| WO | WO 0165948 | 9/2001 |
| WO | WO 2006057520 | 6/2006 |

OTHER PUBLICATIONS

Griffin et al, Transglutaminases: nature's biological glues, Biochem J. Dec. 1, 2002; 368(Pt 2): 377-396.*

Iwami, et al., Amine-binding Capacities of food Proteins in Transglutaminase Reaction and Digestibility of Wheat Gliadin with ε-Attached Lysine, J. Sci. Food Agri,. 1986, 37, 495-503.*

* cited by examiner

TREATMENT OF CEREAL FLOUR AND SEMOLINA FOR CONSUMPTION BY CELIAC PATIENTS

FIELD OF THE INVENTION

The present invention relates to the enzymatic modification of cereal products for food and/or dietetic use.

PRIOR ART

Celiac disease or gluten-sensitive enteropathy is one of the most widespread forms of food intolerance. In genetically susceptible individuals, the disease manifests itself following the ingestion of gliadin which is the major protein constituent of wheat gluten, or of analogous proteins found in other commonly used cereals such as barley, rye and oats. In most cases the intolerance is diagnosed within the first three years of life though there are cases in which it manifests belatedly or is completely asymptomatic. Celiac disease is of great epidemiological importance: in Europe it is calculated that the rate ratio of reported cases is 1:1000 live births, but if latent and asymptomatic cases are also considered, the frequency in reality becomes higher, reaching a rate ratio of 1:200 (Maki et al, 2003). From a clinical viewpoint, celiacs suffer from serious malabsorption syndromes (diarrhoea, weight loss, growth retardation, sideropenic anemia, steatorrhea), while a histological examination of the small intestinal mucosa, where lesions are located, shows hyperplasia of the crypts and varying degrees of atrophy of the intestinal villi.

The unfortunate excess mortality observed with celiacs is not due to malabsorption, however, but to the increased risk of lymphoproliferative disorders, principally intestinal lymphomas. Currently, the only effective therapeutic approach is a completely gluten-free diet, to be followed for life: indeed, only in this way can the normal tissue structure and mucosal functions be recovered and preserved. The strict maintenance of this diet is not easy, however, bearing in mind that small amounts of gluten have been identified in unsuspected food sources and the diet involves rather severe restrictions which justify the efforts directed to finding alternative strategies.

Considerable experimental evidence shows that the mucosal lesions are the product of an altered immune response to gliadin. An analysis of biopsies taken from celiac patients at fasting has highlighted that in these mucosae a massive lymphocyte infiltration exists both in the lamina itself, with a prevalence of CD4$^+$ helper T cells, and in the epithelium above, with largely cytotoxic CD8$^+$ cells. Another important sign of immune activation observed is the increase in cells expressing the interleukin-2 receptor, required for the process of lymphocyte proliferation.

The complete normalization of both the clinical and histological states achieved after removing gluten from the diet, together with the reappearance of all described inflammatory phenomena on subsequent ingestion of just a minimal amount of gluten, provide further evidence that gliadin acts by reversibly activating T lymphocytes which infiltrate the mucosa. In addition, the ability to isolate inflammatory T cell clones from celiac mucosa which respond specifically to gliadin, further corroborates the hypothesis of a cell mediated gliadin-dependent immunological mechanism (Shan et al, 2002).

More recently, the enzymatic deamidation of specific glutamine residues contained in the gliadin molecule has been found to be involved in the induction of the immune response to gluten in celiac subjects. This reaction is carried out by tissue transglutaminase (tTG) present in the intestinal mucosa. It has been demonstrated that the transformation of glutamine into glutamic acid by tTG increases the binding affinity of gluten fragments for the HLA histocompatibility molecules associated with celiac disease (Molberg et al, 1998), i.e. HLA-DQ2, expressed by 95% of celiac patients, and HLA-DQ8, expressed by the remaining 5%. Specifically, the increased binding affinity is believed to be due to the presence of a new negative charge on the gliadin peptide. The deamidated gliadin peptide-histocompatibility molecule complex, exposed on the surface of antigen presenting cells, interacts with receptors on the surface of gliadin-specific T lymphocytes and activates them, with consequent lymphocyte proliferation and secretion of inflammatory cytokines responsible for the mucosal damage (van de Wal et al, 1997; Kim et al, 2004).

Therefore, although the molecular mechanisms at the basis of celiac disease are becoming ever clearer, the need is ever more felt in this sector for providing cereal products that are nontoxic to celiacs. In this respect, dietetic products for gluten-sensitive people are currently prepared exclusively with flour derived from rice or maize.

Various treatments have hitherto been attempted to enable celiacs to consume "toxic" cereals, although these start from a very different approach to that of the authors of the current invention, namely in vivo detoxification of immunoreactive peptides in the patient himself, by way of a therapeutic method i.e. administering molecules able to act in this context. An example of this approach is that proposed in WO99/56698 or that suggested in Matysiak-Budnik et al., Gastroenterology, 2005, 129: 786-796 which proposes the administration of oral enzymes together with gliadin or gluten consumption.

The approach of the invention is completely different i.e. it allows products to be treated and to be detoxified before their consumption by celiacs, by using the enzyme transglutaminase (protein-glutamine: amine γ-glutamyl-transferase, EC 2.3.2.13) whose bacterially derived form (mTG) is already used in the food industry. This enzyme (mTG) is already in use for cereal based products, or derivatives thereof to increase the compactness of the treated product (Collar et al, 2005). Other uses of mTG include its use for increasing, the nutritional value of gluten by the introduction of lysine or dipeptides of lysine (Yokoyama, 2004).

Figure 1:
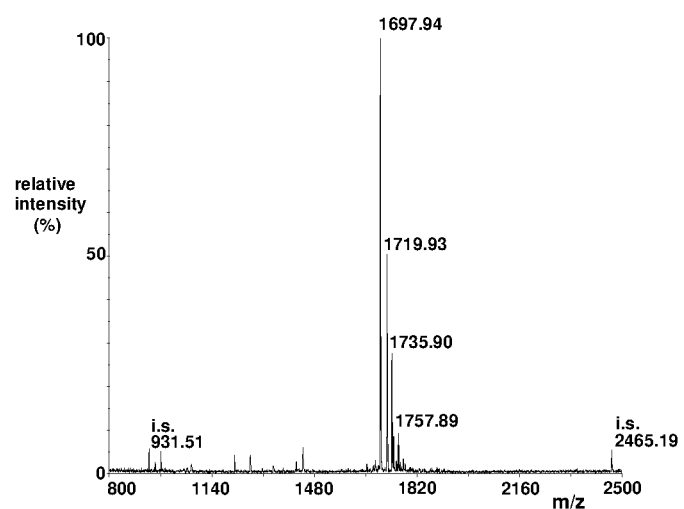
FIG. 1. Mass spectrum MALDI-TOF of the 56-68 peptide of α-gliadin after transamidation with lysine. The satellite ions are due to sodium and potassium adducts.

LEGEND OF SYMBOLS ctrA, flour treated with mTG alone; ctrB, untreated flour; K, flour treated with mTG and lysine; $CH_3$—K, flour treated with mTG and methyl ester of lysine; +tTG, the PT-gliadin produced after treatment of flour is subjected to deamidation with tTG. No difference in terms of treatment effectiveness emerged between the two reaction conditions tested: a) 2 hours at ambient temperature with 20 mM lysine or methyl ester of lysine; b) 4 hours at 37° C. with 2M lysine or methyl ester of lysine.

The results given in the figure represent the mean±SD for the results obtained on testing the 12 lymphocyte cell lines defined in Table 1; the experiments for each line were repeated at least 3 times. The results were analysed by ANOVA and Tukey's test to verify the statistical significance ($P<0.05$). *: different from ctrB+tTG; #: different from K+tTG.

SUMMARY

The present invention relates to a method for treating cereal products and their derivatives containing prolamin, comprising an enzymatic treatment with transglutaminase (amine γ-glutamyl-transferase EC 2.3.2.13) under conditions that favour transamidation of the glutamine residues in a peptide chain lowering the efficiency of a concomitant deamidation. In particular the treatment relates to prolamins which comprise or consist of gluten and/or gliadin.

Both tissue and microbial transglutaminases can be used, either of extractive or recombinant nature, but preferably being food-grade. The reaction takes place in the presence of an alkylated derivative of lysine or of a primary amine: preferably said alkylated derivative of lysine comprises a short chain $C_1$-$C_4$ alkyl and is preferably an alkyl, preferably methyl, ester of lysine. The method is particularly suitable for eliminating the toxicity, for celiac patients, of cereal products and derivatives of oats, wheat, barley, rye and is also applicable directly to flour or to semolina.

The method therefore is usable industrially to detoxify flour before being used in the preparation of food and/or dietetic products.

DETAILED DESCRIPTION OF THE INVENTION

The invention relates to a method that uses the catalytic activity of transglutaminase (protein-glutamine: amine γ-glutamyl-transferase EC 2.3.2.13), preferably microbial transglutaminase, to modify prolamins derived from cereals so as to lower the immunostimulatory capacity of some types of prolamins towards intestinal T lymphocytes of celiac patients, responsible for gluten-sensitive enteropathy.

The procedure is particularly advantageous because it can be implemented directly on flour and semolina which, after being modified and detoxified, are used for preparing food products.

The process of the present invention exploits a property of the transglutaminase enzyme, identified for the first time by the present inventors, which is activated by using the enzyme in the presence of a substrate (i.e. the prolamin to be modified, present in flour or in the cereal derivative) and of an alkylated derivative of lysine, preferably under basic conditions.

The transglutaminase enzyme normally catalyses the acyl transfer reaction between residues of lysine and glutamine within a protein chain, hence leading to the formation of intermolecular isopeptide bonds which are important in various biological processes such as blood clot formation.

The inventors have identified the reaction conditions under which the transglutaminase enzyme in the presence of a non-proteic amino group donor (i.e. free) drives the high efficiency transamidation with formation of an isopeptide bond while at the same time virtually rendering the efficiency of the parallel deamidation reaction equal to zero.

This capacity was first verified by using a mammalian (guinea pig) tissue transglutaminase (tTG) on a peptic-tryptic digest of gliadin under reaction conditions favouring a transamidation reaction (with formation of isopeptide bond) rather than a deamidation reaction.

These conditions are mainly the presence of an alkylated derivative of lysine or a donor of free alkylated amino groups, in the case of tTG, together with preferably an alkaline pH (above 7.5, preferably between 8 and 9). Subsequently, the method was established directly on wheat flour using microbial transglutaminase (mTG), being a food-grade enzyme, and an amino group donor, such as a primary amine or a lysine derivative, preferably an alkylated derivative of lysine, even more preferably a methyl ester of lysine.

Therefore a preferred aspect of the invention relates to a method for the treatment of farinaceous cereal products (flour and semolina) and their derivatives which comprises an enzymatic treatment with transglutaminase under conditions that favour the transamidation of amino acid residues of a prolamin compound and render to zero the efficiency of the deamidation reaction. Said conditions are the presence of a donor of alkylated amino groups such as a primary amine or a lysine derivative, preferably an alkylated derivative of lysine, even more preferably a methyl ester of lysine.

According to the present invention, the term "cereal products" means farinaceous products, semolina of various grades obtained from cereals preferably wheat, barley, rye and oats. Also included are derivatives of said cereals, obtained by s chemical or physicochemical treatment of flour, semolina, whole grains or comminuted grain, such as protein extracts comprising gluten and/or gliadin, peptic-tryptic digests or wheat starch which can contain gluten as contaminant.

The method becomes extremely interesting when prolamin product comprises gluten and/or gliadin in that the treatment of the present invention blocks the highly immunoreactive fractions of cereal products responsible for celiac disease.

Without being restricted by any theory, but only for completeness, it has been observed that in the celiac patient endogenous tissue transglutaminase (tTG), in the absence of primary amines or under specific pH conditions, can deamidate glutamine residues into glutamic acid, introducing negative charges into the molecule. These negative charges increase binding affinity of gliadin to HLA molecules, so that the gliadin fragments are presented more efficiently to T lymphocytes hence triggering the inflammatory process which forms the basis of the CD intestinal pathology (Sollid and Khosla, 2002).

At first, the lowered immunostimulatory capacity of gliadin achieved with the procedure of the invention was verified in various experimental systems using transglutaminase of different origins, then optimised for treating products for food use.

In the experimental systems used, such as a peptic-tryptic digest of gliadin, both the guinea pig tTG enzyme and the microbial transglutaminase (mTG) gave comparable results. In the same experimental system it was also found that simply the presence of an amino group donor such as the amino acid lysine is not a sufficient condition for completely suppressing the immunostimulatory activity of the toxic prolamins (Anderson et al., 2000), though at the alkaline pH values used no trace of the deamidated form occurred. In this respect it is only in the presence of alkylated derivatives of amino group donors, preferably an alkyl ester of lysine, even more preferably a methyl ester of lysine, that a single molecular form corresponding to isopeptide is obtained, said form being devoid of any immunostimulatory activity on cells derived from celiac patients.

These results indicate that transglutaminase can be used in total safety even at alkaline pH in order not to generate highly immunoreactive deamidated gliadin molecules as a by-product of the transamidation reaction. The current finding therefore is a surprising result compared to that reported in the literature (Anderson et al. 2000).

Since the principle whereby prolamins other than gliadin are toxic to particularly sensitive individuals is the same, the invention also extends to prolamins other than gliadin which can be treated under the same reaction conditions identified in the present patent and whose toxicity can be completely lowered by the method of the invention.

According to the method of the invention and based on the experimental confirmations shown, tissue transglutaminases (tTG) from other animal (Sano et al 1996), plant (Serafini-Fracassini and Del Duca, 2002) and microbial (mTG) (Iranzo et al 2002) sources can be used. Microbial transglutaminases, such as those described in Yokoyama K. et al., 2004, are preferred: in this respect they have the advantage of not requiring $Ca^{++}$ as co-factor.

Particularly preferred is the mTG of *Streptomyces mobarensis* which can be extractive or recombinant (Zhu et al, 1995) and which exists in food-grade form. Other mTGs are usable, although mTGs which have lysine as the natural substrate are preferred. The enzyme is used in quantities normally employed by the expert of the art, preferably in quantities of about 1-10 U/g of substrate.

The enzymatic reaction with mTG proceeds for at least one hour at a temperature above 4° C., or, preferably, at a temperature above 25° C. In accordance with a preferred embodiment the product to be treated is dissolved in an aqueous suspension, in the case of flour, at concentrations not higher than 300 mg/ml.

With mTG in particular, deamidation activity was found to be absent even in non-alkaline conditions. It was also found that mTG exhibits the same site-specificity as tTG. Accordingly, mTG is able to drive the transamidation reaction precisely on the same specific glutamine residues which would otherwise be deamidated in the intestine of the celiac, thus triggering the immune response.

The amino-groups donor is preferably an alkylated derivative of lysine, being preferably an alkyl ester of lysine, among which, short chain $C_1$-$C_4$ alkyls are particularly preferred. The alkyl ester of lysine is added or dissolved in quantities of between 5 and 200 mM.

Particularly preferred are "substrates", comprising with the term: "flour", prolamin extracts or purified proteins comprising gluten, avenin, hordein or secalin and hence, more generally, any derivative of wheat, oats, barley, rye preferably in the form of flour, semolina, powder or granules, for food use.

As already previously highlighted, the method can be implemented directly on the flour, semolina or extracts to be detoxified. It has been already reported in the literature that mTG treatment produces high quality flour which maintain optimum organoleptic, viscoelastic and mechanical qualities (Collar, 2005).

In accordance with a particularly preferred aspect, the direct treatment of a food product can be subdivided into the following steps:

dissolution or dilution of the compound to be detoxified (enzymatic digest, flour, semolina, solution) in ratios which are preferably deducible from the following optimal experimental conditions: 1.2 g of commercial wheat flour suspended in 3-ml of water or aqueous buffer containing about 1-10 U mTG (transglutaminase);

addition of an amino-group donor as aforedefined, being preferably a lysine alkylated derivative or, preferably, a lysine alkyl ester derivative, preferably at a concentration between 5 and 200 mM in the case of the methyl ester of lysine;

incubation at 20-40° C. for at least 1-2 hours with optional agitation should the substrate be a powder or semolina;

optional precipitation or purification, for example by phases separation (liquid and solid).

The products obtained from the reaction are chemically modified and also exhibit antigenic properties different from those of untreated products or products treated in other conditions, and are found to be less able or completely unable to stimulate the lymphocytes of celiac patients in vitro. As demonstrated experimentally over the course of the current patent application, they have at least one glutamine residue, residing in the peptide corresponding to the p58-68 α-gliadin fragment which is involved in the isopeptide bond with lysine containing an alkyl group in the α position.

The chemical modifications induced in the peptide corresponding to the p58-68 α-gliadin fragment (transamidation in the presence of alkyl ester) can be monitored by mass spectrometry where the presence of a strong signal at 1697.94 m/z is detected with a mass shift of 129 kDa relative to the theoretical m/z value of the p56-86 peptide as such. In a similar way the presence of a single molecular form corresponding to the isopeptide can be detected.

Said modification is also demonstrable in gliadin-corresponding peptides of prolamins other than gliadin, such as: avenin and/or hordein and/or secalin which are transamidated and involved in an isopeptide bond. The present invention comprises, therefore, products derived and obtainable in accordance with the described process as well as food products containing the modified prolamins as aforedescribed.

The enzymatic reaction conditions, in the presence of alkylated derivatives of lysine and where there is a total absence of deamidated contaminants, can be extended to other uses of tissue or microbial transglutaminase where a higher efficiency of transamidation rather than deamidation is preferable. Therefore the invention extends to the use of a transglutaminase (amine γ-glutamyl-transferase EC 2.3.2.13), preferably under alkaline conditions (pH higher than 7.5, preferably between 8 and 9) in the case of tissue transglutaminase (tTG), in the presence of an alkylated derivative of lysine for a high efficiency transamidation and binding through an isopeptide bond of glutamine amino acid residues.

The method of the invention is industrially applicable to all processes for preparing specialty or dietetic food products formulated for gluten-sensitive individuals, and comprises a treatment for cereal flour, semolina or derivatives or their mixtures as aforedescribed, in particular using the food-grade enzyme (mTG).

Experimental Part

Materials and Methods

Preparation of a Peptic-Tryptic Digest of Gliadin (PT-Gliadin).

20 mg of gliadin are suspended in 200 μl of 0.2 N HCL pH 1.8 in the presence of pepsin (protein:enzyme ratio 100:1) and incubated for 4 hours at 37° C. The pH is then brought to 8.5 by adding Tris (final concentration 0.125 M). Trypsin is added to the solution (protein:enzyme ratio 100:1) and the incubation at 37° C. proceeds for a further 2 hours. The reaction is finally stopped by boiling the sample for 10 minutes. The samples are stored at −20° C. until required.

Deamidation of PT-Gliadin.

2 mg of PT-gliadin are suspended in 1 ml of 0.125 M Tris/HCL pH 8.5 containing 1 mM calcium chloride, 10 mM dithiotreitol and 200 μg of tTG. The reaction is carried out at 37° C. for 4 hours, then stopped by boiling the sample for 10 minutes. Samples are stored at −20° C. until required.

Transamidation of PT-Gliadin.

PT-gliadin (2 mg) and lysine or methyl ester of lysine (20 mM) are suspended in 1 ml of 0.125 M Tris/HCL pH 8.5 containing 1 mM calcium chloride, 10 mM dithiotreitol and 200 μg tTG. The reaction is carried at 37° C. for 4 hours, then stopped by boiling the sample for 10 minutes. The samples are stored at −20° C. until required.

Analysis by Mass Spectrometry MALDI-TOF.

The transamidation reaction is monitored using a synthetic α-gliadin peptide (residues 56-68, LQLQPFPQLPY) as a model. After the reaction the mass spectra are acquired by accumulating 100 laser shots, using as internal standards the monoisotopic peaks of angiotensin (m/z 931.5154) and of ACTH (m/z 2465.1989) so as to reduce experimental error to less than 20 ppm; the values are reported as monoisotopic masses.

Enzymatic Treatment of Flour.

1.2 g of commercial wheat flour are suspended in 10 ml of water containing 8 U mTG (N-Zyme Biotec GMbH, Darmstadt, Germany) and 20 mM or 2 M lysine or methyl ester of lysine; the reaction is carried, at room temperature for 2 hours or for 4 hours at 37° C.

Extraction of Gliadin.

The aqueous flour suspension is transferred into 67 mM sodium phosphate buffer pH 7.6 containing 0.4 M NaCl and extracted by agitating for 30 minutes followed by centrifugation for 15 minutes at 15,500 g. The pellet is recovered and resuspended in 20 ml of an aqueous ethanol solution (70%) and extracted by agitation for 45 minutes, followed by centrifugation for 15 minutes at 15,000 g. The supernatant consisting of gliadin is then lyophilized and stored at −20° C. until required.

Generation of Gliadin-Specific Intestinal T-Lymphocyte Lines.

Twelve consenting HLA-DQ2+ adult celiac patients, eight of whom were treated with diet (age range 18-49, mean 29.49) and 4 untreated (age range 18-34, mean 27), were enrolled in the study. Mucosal biopsies from these patients at fasting were digested with collagenase A. The intestinal cells were suspended in RPMI culture medium supplemented with antibiotics, non-essential amino acids, sodium pyruvate, glutamine and inactivated human serum (10%) at a density of $2 \times 10^5$/ml. The cells were then stimulated with irradiated (3500 Rad) autologous peripheral blood cells (PBMCs; $1 \times 10^6$/ml) and PT-gliadin deamidated by treatment with tTG (50 μg/ml). Twenty-four hours later fresh medium containing 10 ng/ml IL-15 was added to the cultures. On day 7 the intestinal T cell lines (iTCLs) produced were again stimulated with antigen and PBMCs followed by addition of fresh medium and IL-15 on the following day and at 3-4 day intervals. All the iTCLs obtained were found to be positive for CD4 molecule expression.

Analysis of the iTCLs.

The T cell lines were tested while in the resting phase using transformed B-lymphoblastoid cells, from the same HLA haplotype, as antigen presenting cells (APCs). Irradiated APCs ($5 \times 10^5$/ml) were incubated for 18 hours with PT-gliadin (50 μg/ml) in 96-well plates. The iTCLs ($1.5 \times 10^5$/ml) were added into each plate at a final volume of 200 μl. After 48 hours of incubation aliquots of the supernatant were collected to determine the IFNγ production (inflammatory marker) by ELISA.

Example 1

Characterization of Structural Modifications Induced on the Peptide by Enzymatic Treatment With the aim of determining the structural modifications induced by transglutaminase, a synthetic α-gliadin peptide p56-68 containing an immunodominant epitope of gliadin (Shan et al 2002) was incubated in the presence or absence of lysine or methyl ester of lysine and tTG. The modifications induced by the reaction were monitored by mass spectrometry. It can be seen that p56-68 reacts with lysine giving rise to a strong signal at m/z 1697.94 (FIG. 1) with a mass shift of 129 KDa with respect to the theoretical m/z value of the peptide as such. Of note at the used alkaline pH values, no trace of the deamidated form is detected. Similarly only one molecular form, corresponding to the isopeptide, is formed following enzymatic treatment under alkaline conditions with the methyl ester of lysine. These results therefore indicate, in contrast to that reported in the literature (Anderson et al. 2000), that transglutaminase can be safely used at alkaline pH so as not to generate highly immunoreactive deamidated gliadin molecules as a by-product of the transamidation reaction, and in particular that, under alkaline conditions, transglutaminase converts 100% of substrate into its transamidated form. Similarly, mTG was observed not to generate deamidation products even in non-alkaline conditions.

Example 2

Assessment of IFN-γ Production by Lymphocytes of Celiac Patients Following Stimulation with the Peptides Modified According to the Invention or to the Prior Art Transamidation is able to inhibit the immune response towards gliadin in vitro. The ability of the transamidation reaction under alkaline conditions, to inhibit the immune response to gliadin is evaluated by using iTCLs derived from celiac patients. The iTCLs are incubated in the presence of a peptic-tryptic digest of wheat gliadin (PT-gliadin) treated with tTG in the presence or absence of an amino group donor. The results relating to the production of IFNγ secreted in the culture supernatant are given in Table 1. All the iTCL lines show the ability to specifically produce inflammatory cytokine following stimulation with deamidated PT-gliadin; some samples produce a good response even in the presence of native PT-gliadin, probably due to non-specific deamidation induced by acid treatment during pepsin digestion. Of note, the transamidation reaction under alkaline conditions is able to lower cytokine production, except for sample CD2.

Example 3

Optimization of the Transamidation Reaction

Surprisingly, a comparison of the results obtained with lysine and methyl ester of lysine shows unequivocally that this latter is more effective in inhibiting IFNγ production, reducing values to the negligible baseline levels reported for medium alone for a large part of the tested samples, except for CD2 (Table 1). The cell line isolated from this patient also reacts well to non-deamidated gliadin (see table) and this can explain the ineffectiveness of the transamidation reaction for this sample. Taken together the data suggest that the residual negative charge of the carboxylic group of lysine, bound to glutamine through an isopeptide bond, still determines a certain degree of affinity for the HLA molecule, whereas the presence of a methyl group cancels out the charge hence reducing the interaction in an optimal manner.

TABLE 1

IFNγ production assessed in the culture supernatant of iTCLs from celiac patients following stimulation with PT-gliadin preparations treated with tTG

| | | IFNγ[1,2] | | | |
|---|---|---|---|---|---|
| iTCL | Medium | Native PT-gliadin | Deamidated PT-gliadin | PT-gliadin-lysine alkaline pH | PT-gliadin-methyl ester of lysine |
| CD1 | <ls[3] | 7 | 100 | 54 | 25 |
| CD2 | 2 | 76 | 100 | 105 | 99 |
| CD3 | 0 | 3 | 100 | 2 | 0 |
| CD4 | <ls | 20 | 100 | 2 | <ls |
| CD5 | 11 | 19 | 100 | 14 | 9 |
| CD6 | 3 | 42 | 100 | 63 | 16 |
| CD7 | 0 | 9 | 100 | 58 | 28 |
| CD8 | 1 | 14 | 100 | 17 | 8 |
| CD9 | <ls | 23 | 100 | 13 | <ls |
| CD10 | <ls | | 100 | <ls | <ls |
| CD11 | 2 | 24 | 100 | 25 | 7 |
| CD12 | <ls | 19 | 100 | 34 | 3 |

[1]The values refer to 1 × 10[6] cells and are expressed in percentage terms relative to the production induced by deamidated PT-gliadin
[2]Limit of ELISA sensitivity: 62.5 pg/ml
[3]<ls: below the limit of test sensitivity From the data in table 1 it can be concluded that PT-gliadin reactivity is lowered by the transamidation reaction under alkaline conditions, but that a drastic inhibition of the inflammatory response to gliadin only occurs with transamidation in the presence of the methyl ester of lysine, rather than lysine, as a donor of amino-groups.

Example 4

Lowering the Immunoreactivity of Gluten in Cereal Flour by Direct Treatment with mTG Based on the previous results obtained with gliadin preparations the feasibility of directly transamidating flour from toxic cereals with methyl ester of lysine has been assessed. The tTG enzyme cannot essentially be used for this purpose because it is not food-grade, it has high production costs and a high molecular weight (76 kDa) making interaction on a complex food matrix difficult. In view of this, microbial transglutaminase (mTG) is of particular interest, being an already widely used enzyme in the food industry for improving the quality of meat, fish, milk and soya based products (Zhu et al. 1995; Motoki and Seguro 1998). A further advantage of this enzyme is that it does not require calcium as co-factor and it is small in size (MW 38 kDA) thus enabling its potential interaction with glutamine residues even under native conditions.

Figure 2:
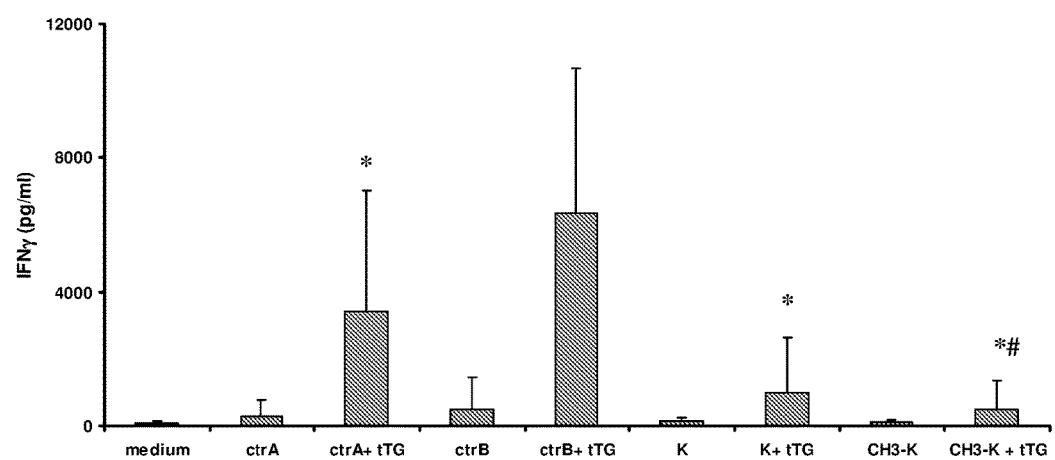
FIG. 2. Production of IFNγ by iTCLs (intestinal T cell lines) after stimulation with PT-gliadin isolated from flour subjected to treatment with mTG±lysine or methyl ester of lysine.

According to the above, we incubated an aqueous suspension of commercial flour in the presence of mTG and lysine or methyl ester of lysine under two different reaction conditions: a) 2 hours at ambient temperature with or without lysine or methyl ester of lysine 20 mM; b) 4 hours at 37° C. with or without lysine or methyl ester of lysine 2 M. At the end of the incubation the gliadin fraction was extracted as described in Materials and Methods. The gliadin was then digested with pepsin and trypsin (PT-gliadin). The PT-gliadin preparation was subdivided into two batches one of which was subjected to deamidation reaction with tTG. The different preparations were finally subjected to in vitro testing with the iTCLs. The results, given in FIG. 2, relate to the treatment according to protocol a); in this respect no differences were found in terms of efficiency between protocols a) and b). Surprisingly, mTG was found to be able to drive a transamidation reaction which inhibits the immunostimulatory activity of gliadin. It can be seen that, as with the previous data obtained with PT-gliadin using tTG, transamidation with the methyl ester of lysine is found to be statistically more efficient than lysine in reducing the inflammatory response (FIG. 2). The final mean values of IFNγ production obtained after treatment with the methyl ester of lysine and mTG are close to baseline values.

It can therefore be confirmed that pre-treating flour with microbial transglutaminase and methyl ester of lysine lowers the immunostimulatory properties of gliadin even when flour is directly treated.

Electrophoretic analysis of gliadin extracted from flour after enzymatic treatment also indicates that substantial changes in the molecule such as to impair its function in technological processes are not present.

In conclusion the data obtained fully confirm the validity of the present invention as a pre-treatment method for flour, semolina or protein extracts with the aim of reintroducing "toxic" cereals into the diet of celiacs.

BIBLIOGRAPHY

Anderson, R. P., P. Degano, A. J. Godkin, D. P. Jewell, and A. V. Hill. 2000. In vivo antigen challenge in celiac disease identifies a single transglutaminase-modified peptide as the dominant A-gliadin T-cell epitope. *Nat. Med.* 3: 337-342.

Collar, C., C Bollain, A. Angioloni. 2005. Significance of microbial transglutaminase on the sensory, mechanical and crumb grain pattern of enzyme supplemented fresh pan breads. *J. Food Eng.* 70; 479-488.

Iranzo M, Aguado C, Pallotti C, Canizares J V, Mormeneo S. Transglutaminase activity is involved in Saccharomyces cerevisiae wall construction. Microbiology. 2002 May; 148 (Pt 5):1329-34.

Kim, C. Y., H. Quarsten, E. Bergseng, C. Khosla, and L. M. Sollid. 2004. Structural basis for HLA-DQ2 mediated presentation of gluten epitopes in celiac disease. *Proc. Natl. Acad. Sci. USA* 101: 4175-4179.

Maki, M., K. Mustalahti, J. Kokkonen, P. Kulmala, M. Haapalahti, T. Karttunen, J. Ilonen, K. Laurila, I. Dahlbom, T. Hansson, P. Hopfl, and M. Knip. 2003. Prevalence of Celiac disease among children in Finland. *N. Engl. J. Med.* 348: 2517-2524.

Molberg, O., S. N. McAdam, R. Korner, H. Quarsten, C. Kristiansen, L. Madsen, L. Fugger, H. Scott, O. Noren, P. Roepstorff, K. E. Lundin, H. Sjostrom, and L. M. Sollid. 1998. Tissue transglutaminase selectively modifies gliadin peptides that are recognized by gut-derived T cells in celiac disease. *Nat. Med.* 4: 713-717.

Motoki, M., and K. Seguo. 1998. Transglutaminase and its use for food processing. *Trends Food Sci. Technol.* 9: 204-210.

Quarsten, H., O. Molberg, L. Fugger, S. N. McAdam, and L. M. Sollid. 1999. HLA binding and T cell recognition of a tissue transglutaminase-modified gliadin epitope. *Eur. J. Immunol.* 29: 2506-2514.

Sano K, Nakanishi K, Nakamura N, Motoki M, Yasueda H. Cloning and sequence analysis of a cDNA encoding salmon (Onchorhynchus keta) liver transglutaminase. Biosci Biotechnol Biochem. 1996 November; 60(11):1790-4.

Serafini-Fracassini D, Del Duca S (2002) Biochemistry and function of plant transglutaminases. *Minerva Biotec* 14:135-141.

Shan, L., O. Molberg, I. Parrot, F. Hausch, F. Filiz, G. M. Gray, L. M. Sollid, and C. Khosla. 2002. Structural basis for gluten intolerance in celiac sprue. 2002. *Science* 297: 2275-2279.

Sollid L. M. 2002. Celiac disease: dissecting a complex inflammatory disorder. *Nat. Rev. Immunol.* 2: 647-655.

van de Wal, Y., Y. M. Kooy, J. W. Drijfhout, R. Amons, G. K. Papadopoulos, and F. Koning. 1997. Unique peptide binding characteristics of the disease-associated DQ(alpha 1*0501, beta 1*0201) vs the non-disease-associated DQ(alpha 1*0201, beta 1*0202) molecule. *Immunogenetics* 46: 484-492.

Yokoyama, K., N. Nio, and Y. Kikuchi. 2004. Properties and applications of microbial transglutaminasi. *Appl Microbiol Biotechnol* 64: 277-282

Zhu, Y., A. Rinzema, J. Tramper, and J. Bol. 1995. Microbial transglutaminase—A review of its production and application to food processing. *Appl Microbiol Biotechnol* 44: 277-282.

The invention claimed is:

1. A process for obtaining cereal products suitable for gluten-sensitive individuals, the process comprising the steps of:
   a. providing a cereal product comprising gliadin and gluten, both the gliadin and the gluten having glutamine residues;
   b. treating the glutamine residues of the gliadin and the gluten with a $C_1$-$C_4$ alkyl ester of lysine in the presence of a transglutaminase, said transglutaminase being an amine γ-glutamyl-transferase EC 2.3.2.13.

2. The method according to claim 1 wherein said transglutaminase is tissue or microbial transglutaminase.

3. The method according to claim 2 wherein said transglutaminase is extractive or is recombinant transglutaminase.

4. The method according to claim 2 wherein said transglutaminase is food-grade.

5. The method according to claim 2 wherein said transglutaminase is microbial transglutaminase.

6. The method according to claim 1 wherein said cereal products comprises gluten and/or gliadin.

7. The method according to claim 1 wherein said cereal product is selected from the group consisting of: oats, wheat, barley or rye.

8. The method according to claim 7 wherein the product is in the form of flour or semolina.

9. The method according to claim 1 wherein said cereal product is selected from the group consisting of: gliadin, avenin, hordein or secalin.

10. The method according to claim 9 wherein said product comprises grain starch.

11. The method according to claim 7 further comprising a step of preparation of a food product.

12. The method of claim 11 wherein said food product is suitable for gluten-sensitive individuals.

13. The method according to claim 1 wherein said alkyl ester is a methyl ester of lysine.

* * * * *